United States Patent [19]
Gustafsson et al.

[11] Patent Number: 6,120,485
[45] Date of Patent: *Sep. 19, 2000

[54] ABSORBENT PANTS PRODUCT

[75] Inventors: Anders Gustafsson, Billdal; Urban Widlund, Mölnlycke, both of Sweden

[73] Assignee: SCA Hygiene Products AB, Goteborg, Sweden

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/875,629

[22] PCT Filed: Feb. 1, 1996

[86] PCT No.: PCT/SE96/00119

§ 371 Date: Sep. 29, 1997

§ 102(e) Date: Sep. 29, 1997

[87] PCT Pub. No.: WO96/23467

PCT Pub. Date: Aug. 8, 1996

[30] Foreign Application Priority Data

Feb. 2, 1995 [SE] Sweden .................................. 9500385

[51] Int. Cl.[7] ..................................................... A61F 13/15
[52] U.S. Cl. ............................... 604/385.19; 604/385.22; 604/388.25; 604/385.29; 604/385.3; 604/397; 604/398
[58] Field of Search ............................... 604/385.1, 385.2, 604/393–396, 327, 329, 346–348, 397–398, 385.19, 385.22, 385.25, 385.29, 385.3

[56] References Cited

U.S. PATENT DOCUMENTS

| | | | |
|---|---|---|---|
| 1,695,109 | 12/1928 | Kosloff . | |
| 2,069,092 | 1/1937 | Jackson, Jr. | 604/397 |
| 2,538,758 | 1/1951 | Bricmont | 604/347 |
| 3,532,093 | 10/1970 | Lovret | 604/348 |
| 3,890,973 | 6/1975 | Davis et al. . | |
| 4,044,769 | 8/1977 | Papajohn | 604/385.2 |
| 4,285,342 | 8/1981 | Mesek | 604/389 |
| 4,421,512 | 12/1983 | Papajohn . | |
| 4,662,877 | 5/1987 | Williams | 604/385.2 |
| 4,886,508 | 12/1989 | Washington | 604/347 |
| 4,892,536 | 1/1990 | Des Marais et al. . | |
| 5,037,416 | 8/1991 | Allen et al. | 604/385.2 |
| 5,062,840 | 11/1991 | Holt et al. | 604/385.1 |
| 5,207,603 | 5/1993 | McQueen | 604/385.2 |
| 5,817,086 | 10/1998 | Kling | 604/385.2 |
| 5,928,211 | 7/1999 | Gustafsson et al. | 604/385.2 |

FOREIGN PATENT DOCUMENTS

| | | | |
|---|---|---|---|
| 0357298 | 3/1990 | European Pat. Off. . | |
| 0626160 | 5/1994 | European Pat. Off. | 604/385.2 |
| 0 026 160 | 11/1994 | European Pat. Off. | 604/385.2 |
| 3186262 | 8/1991 | Japan | 604/385.2 |
| 405285168 | 11/1993 | Japan | 604/385.2 |
| 2022026 | 11/1991 | Spain . | |
| 2268073 | 1/1994 | United Kingdom . | |
| 2 297 473 | 6/1996 | United Kingdom . | |
| 97146197 | 12/1997 | WIPO . | |

OTHER PUBLICATIONS

Translation of Spanish Patent No. 2,022,026, Apr. 17, 1998.

*Primary Examiner*—John G. Weiss
*Assistant Examiner*—K. M. Reichle
*Attorney, Agent, or Firm*—Burns, Doane, Swecker & Mathis, L.L.P.

[57] ABSTRACT

A disposable absorbent pants diaper includes an elastic pant provided with holes corresponding to the locations of the anus and the urethral opening when worn. Liquid impermeable layers cover the holes and are sealed to the elastic pant around the holes to thereby form pockets for receiving feces and urine respectively. The pockets also contain absorbent and/or superabsorbent material.

9 Claims, 2 Drawing Sheets

ABSORBENT PANTS PRODUCT

FIELD OF THE INVENTION

The present invention relates to a disposable absorbent pants product.

BACKGROUND OF THE INVENTION

A disposable diaper product of this type is shown and described in EP-A 357 298, where an inner envelope, which may be a polyolefine sheet with perforations to allow urine to pass through, is provided with an aperture to allow feces to pass through. The envelope is provided with elastic strands to hold it in place against the wearer's body. Outside the elasticized envelope, the diaper is provided with absorbent material and an outer jacket of liquid-impermeable material, which is attached to the inner envelope only at the waist edges and the leg edges of the diaper. When filled with urine and feces, the absorbent material and the outer jacket will hang down between the legs of the wearer, decreasing comfort and security against leakage. When the absorbent material is deformed in the narrow space between the user's legs the elasticized envelope can often be forced away from correct contact with the skin of the user, giving rise to folds and creases and leakage can then occur.

The problem of keeping a diaper in place has been approached in many different ways. Elastic side panels for example are described in EP-A 320 991. SE 425 942 describes the placement of elastic means in a V-shaped pattern to hold the liquid permeable layer of the diaper in better contact with the user's body. Neither of these known solutions is completely satisfactory as regards holding the product in place to prevent leakage and neither of them addresses the problem at all of keeping urine and feces out of contact with the user's skin.

SUMMARY OF THE INVENTION

These problems are satisfactorily solved by a disposable absorbent pants product in accordance with the present invention.

According to the present invention, a disposable absorbent article to be worn by an individual possessing an anus and a urethral opening includes an elastic pant provided with a first hole adapted to be located at the anus of the individual when the article is worn by the individual and a second opening adapted to be located at the urethral opening when the article is worn by the individual. The first hole is separate from the second hole. An outer liquid impermeable cover covers the first hole to form a first pocket for receiving feces, and an outer liquid impermeable cover covers the second hole to form a second pocket for receiving urine.

BRIEF DESCRIPTION OF THE DRAWING FIGURES

The present invention will now be described with reference to examples shown in the accompanying figures of which:

FIG. 1 shows a pant diaper according to the invention in its extended state just prior to final assembly as seen from the inside of the pant diaper, FIG. 2 shows the pant diaper according to the present invention in its extended state just prior to final assembly as seen from the outside, FIG. 3 shows the pant diaper according to the present invention after final assembly as worn by a child.

DETAILED DESCRIPTION OF THE INVENTION

The pant diaper according to the invention as shown in the figures is essentially based on an elastic pant 1 composed of an elastic net or film covered with substantially liquid-permeable and air-permeable, e.g. hydrophobic, layers of non-woven material. The elastic pant is provided with a hole 2 which, when the pant is worn, will be placed directly at the urethral opening. The placement and size of said hole 2 may be adapted to the sex and/or age of the intended wearer. The pant is also provided with a hole 3 which will be placed directly at the anus when worn.

Figure 2:
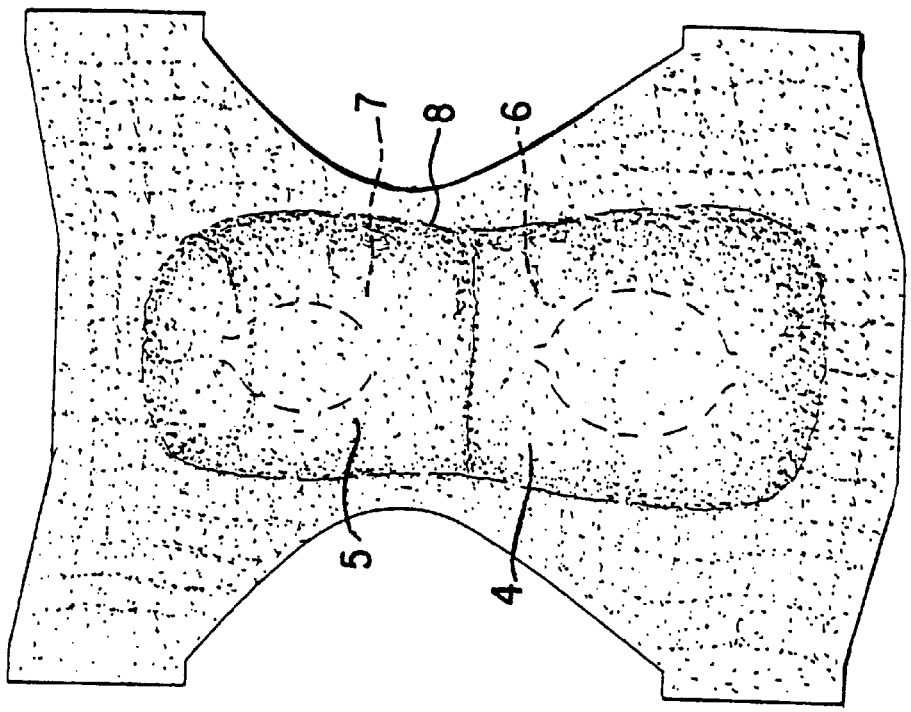
Figure 1:
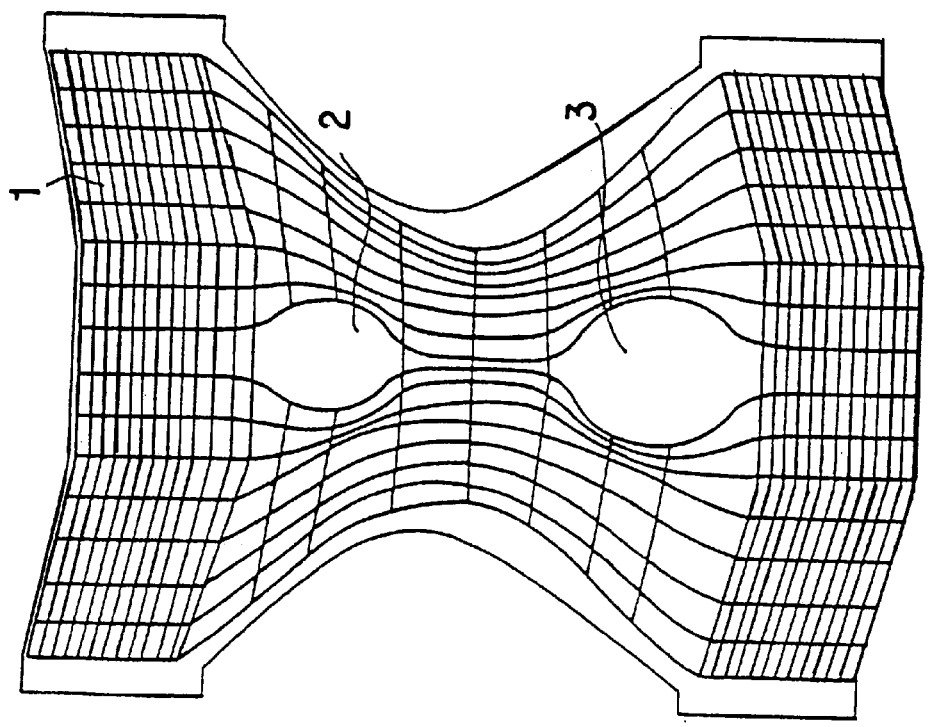
Figure 3:
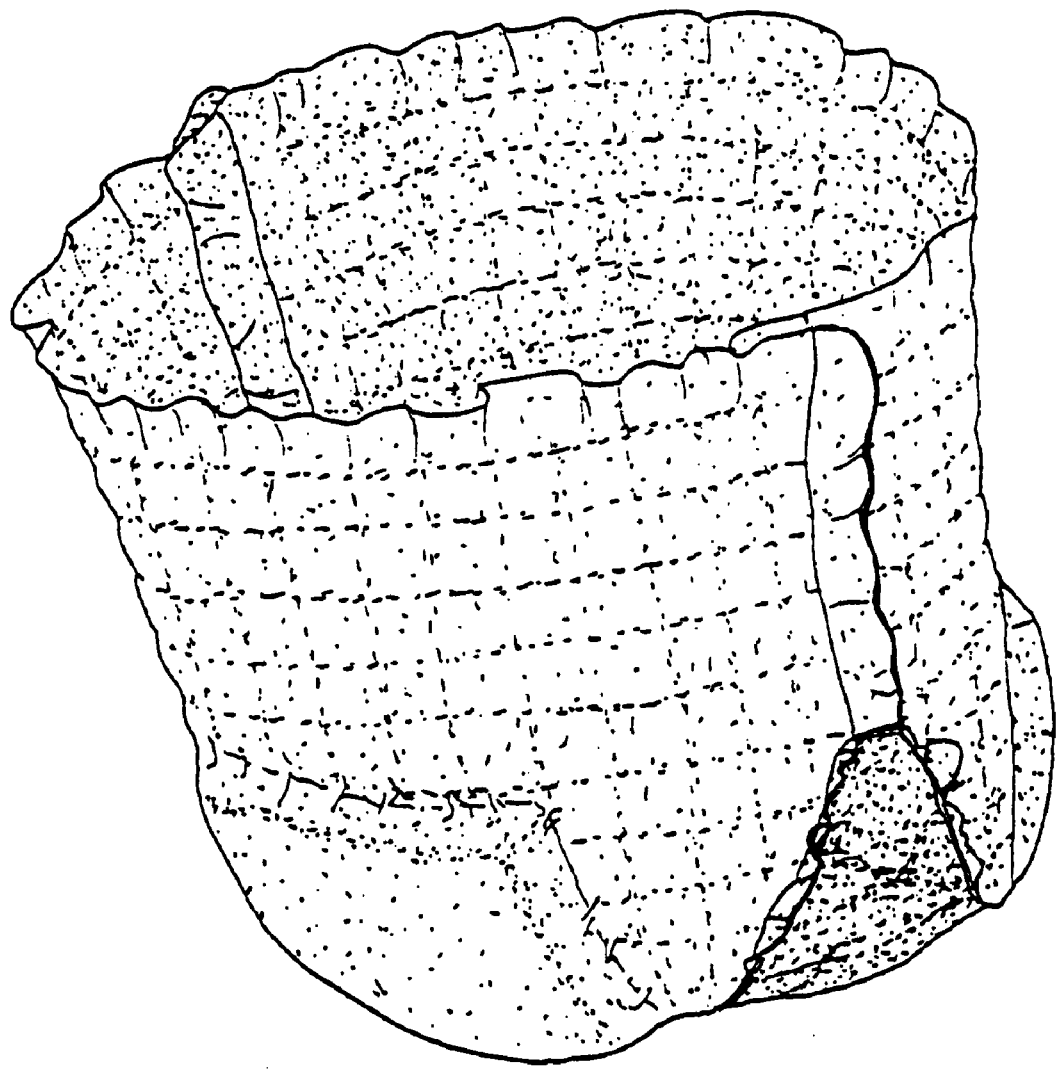

As can be seen most clearly in FIG. 2, cover layers 4, 5 of liquid impermeable material such as polyethylene film or a hydrophobic nonwoven fabric cover each of the holes and are sealingly fixed (as indicated by reference numeral 8) to the elastic pant thereby forming a pocket around each of said holes 3 and 2 respectively. According to preferred embodiments each pocket can be filled with absorbent material 6, 7 such as fluff pulp and/or superabsorbent material, for reception of feces in the back pocket and urine in the front pocket. The absorbent material covers the hole or holes and the area immediately surrounding the hole or holes, and the liquid impermeable layer that covers the absorbent material is sealed to the elastic pant only in the area immediately surrounding the absorbent material. The absorbent material extends circa 1½–2 centimeters beyond the periphery of the respective hole. Thus, the liquid impermeable cover layer 4 that covers the hole 3 also covers the absorbent material 6 that is disposed in the pocket located around the hole 3. Similarly, the liquid impermeable cover layer 5 that covers the hole 2 also covers the absorbent material 7 that is disposed in the pocket located around the hole 2.

The elastic pant is thus held snugly in place against the body of the user. When feces or urine is excreted they will pass through their respective holes, which need not be made particularly large since the elastic pant is held firmly in its proper place, and into their respective pockets. The front pocket may be filled and weighted down with urine without it pulling the elastic pant out of position in contact with the user. And since the pockets are separated from each other the feces and urine will not mix which is a known advantage to prevent leakage and prevent irritation of the skin.

The pockets can be made of elastic material to be able to expand as they are filled with feces or urine.

What is claimed is:

1. A disposable absorbent article to be worn by an individual possessing an anus and a urethral opening, comprising:
   an elastic pant provided with a first hole adapted to be located at the anus of the individual when the article is worn by the individual and a second opening adapted to be located at the urethral opening when the article is worn by the individual, said first hole being separate from said second hole, an outer liquid impermeable cover that covers said first hole to form a first pocket for receiving feces, and an outer liquid impermeable cover that covers said second hole to form a second pocket for receiving urine.

2. A disposable absorbent article according to claim 1, including absorbent material disposed in said first pocket and extending circa 1½–2 centimeters beyond a periphery of the first hole, and an absorbent material disposed in said second pocket and extending circa 1½–2 centimeters beyond a periphery of the second hole.

3. A disposable absorbent article according to claim 1, including absorbent material disposed in said first pocket and said second pocket, said absorbent material covering said first and second holes and an area immediately surrounding said first and second holes, said liquid impermeable cover that covers said first hole also covering said absorbent material in said first pocket, and said liquid impermeable cover that covers the second hole also covering said absorbent material in said second pocket, said liquid impermeable cover that covers said first hole being sealed to said elastic pant only in an area of said elastic pant immediately surrounding said first hole, and said liquid impermeable cover that covers the second hole being sealed to said elastic pant only in an area of said elastic pant immediately surrounding said second hole.

4. A disposable absorbent article according to claim 1, including absorbent material disposed in said first pocket, said liquid impermeable cover that covers said first hole also covering said absorbent material disposed in said first pocket.

5. A disposable absorbent article according to claim 1, including absorbent material disposed in said first pocket and absorbent material disposed in said second pocket, said liquid impermeable cover that covers said first hole also covering said absorbent material in said first pocket, and said liquid impermeable cover that covers the second hole also covering said absorbent material in said second pocket.

6. A disposable absorbent article according to claim 1, including absorbent material disposed in said second pocket, said liquid impermeable cover that covers said second hole also covering said absorbent material in said second pocket.

7. A disposable absorbent article according to claim 1, wherein said liquid impermeable cover that covers the first hole is sealed to said elastic pant in an area of said elastic pant immediately surrounding said first hole, and said liquid impermeable cover that covers the second hole being sealed to said elastic pant in an area of said elastic pant immediately surrounding said second hole.

8. A disposable absorbent article according to claim 1, wherein said liquid impermeable cover that covers said first hole is sealed to said elastic pant only in an area of said elastic pant immediately surrounding said first hole, and said liquid impermeable cover that covers the second hole being sealed to said elastic pant only in an area of said elastic pant immediately surrounding said second hole.

9. A disposable absorbent article according to claim 1, wherein said liquid impermeable cover that covers said first hole is elastic and said liquid impermeable cover that covers said second hole is elastic.

* * * * *